United States Patent
Slatkine et al.

[11] Patent Number: 5,807,386
[45] Date of Patent: Sep. 15, 1998

[54] LASER FACIAL REJUVENATION

[75] Inventors: Michael Slatkine, Herziiah, Israel; Douglass Mead, Allendale, N.J.

[73] Assignee: Laser Industries, Ltd., Tel Aviv, Israel

[21] Appl. No.: 738,305

[22] Filed: Oct. 25, 1996

Related U.S. Application Data

[62] Division of Ser. No. 382,918, Feb. 3, 1995, Pat. No. 5,611,795.

[51] Int. Cl.$^6$ .................................................. A61B 17/36
[52] U.S. Cl. .................................................. 606/9; 606/10
[58] Field of Search .................................. 606/9, 10, 11, 606/12, 14, 16, 17

[56] References Cited

U.S. PATENT DOCUMENTS

| | | | |
|---|---|---|---|
| 3,884,236 | 5/1975 | Krasnov | 606/9 |
| 4,469,098 | 9/1984 | Davi . | |
| 4,566,503 | 1/1986 | Kumano et al. . | |
| 4,587,396 | 5/1986 | Rubin | 219/121 |
| 4,672,969 | 6/1987 | Dew | 128/397 |
| 4,733,660 | 3/1988 | Itzkan . | |
| 4,775,361 | 10/1988 | Jacques et al. | 606/5 |
| 4,917,083 | 4/1990 | Harrington et al. | 606/15 |
| 5,057,104 | 10/1991 | Chess | 606/9 |
| 5,071,417 | 12/1991 | Sinofsky | 606/8 |
| 5,217,455 | 6/1993 | Tan | 606/9 |
| 5,226,907 | 7/1993 | Tankovich | 606/9 |
| 5,280,378 | 1/1994 | Lombardo . | |
| 5,282,797 | 2/1994 | Chess | 606/9 |
| 5,312,395 | 5/1994 | Tan et al. | 606/9 |
| 5,336,217 | 8/1994 | Buys et al. | 606/9 |
| 5,344,418 | 9/1994 | Ghaffari | 606/9 |
| 5,411,502 | 5/1995 | Zair | 606/10 |
| 5,423,803 | 6/1995 | Tankovich et al. | 606/9 |
| 5,464,436 | 11/1995 | Smith | 606/9 |
| 5,474,549 | 12/1995 | Ortiz et al. | 606/11 |
| 5,527,350 | 6/1996 | Grove et al. | 606/9 X |
| 5,582,752 | 12/1996 | Zair | 606/11 X |
| 5,611,795 | 3/1997 | Slatlane et al. | 606/9 |
| 5,624,434 | 4/1997 | Abergel et al. | 606/9 |

FOREIGN PATENT DOCUMENTS

| | | | |
|---|---|---|---|
| 1073914 | 6/1985 | U.S.S.R. | 606/10 |

OTHER PUBLICATIONS

Richard W. Maloney, MD "Laser Otology", Operative Techniques in Otolaryngology Head and Neck Surgery, vol. 3, No. 2, Jun. 1992, pp. 74–83.
I.L. Med. Unilase product info. brochure "The Proven Solution for Disk, Spinal Cord and Brain Microsurgery" (1993).
I.L. Med. Unilase product info. brochure "The Proven Solution for Otologic and Microlaryngeal Surgery" (1993).
"UNILASE A new $CO_2$ Laser for Microsurgery", I.L. Med. Newsletter, vol. 1, No. 3, Spring 1991.
"New Laser for Microlaryngeal Surgery", I.L. Med Newsletter, vol. 1, Spring 1991.
S. George Lesinski, MD and Richard Newrock, Ph.D. "Carbon Dioxide Lasers for Otosclerosis", Otolaryngologic Clinics of North America, vol. 26, No. 3, Jun. 1993.
I.L. Med Unilase System Brochure (1993).
"Using a $CO_2$ Laser During Conventional Microdiskectomy Shows Promise of Faster Recovery", I.L. Med Newsletter, vol. 1, No. 4, Spring 1991.
I.L. Med Magana Diskectomy Microreactor Set, brochure.
Palm Beach Gardens Medical Center First in Nation to Perform Advanced Laser Back Surgery, press release.
I.L. Med UNILASE CO2 Laser information relating to mounts, balancing and drapes.

(List continued on next page.)

Primary Examiner—Jennifer Bahr
Assistant Examiner—Sonya Harris-Ogugua
Attorney, Agent, or Firm—Cobrin Gittes & Samuel

[57] ABSTRACT

A method of facial rejuvenation is provided in which ablation of an area of skin is accomplished to above the papillary dermis, providing effective permanent smoothness. A laser beam directs a laser beam from a laser source to a scanner which directs the beam to ablate the skin.

9 Claims, 1 Drawing Sheet

OTHER PUBLICATIONS

I.L. Med Advertisement suggesting use of the CO2 Laser with the new UNILASE.

Sharplan Lasers, Inc. "Advanced Technology of Aesthetic $CO_2$ Laser Surgery" brochure, published in the United States in Jan. 1995, 2 pages.

Sharplan Lasers, Inc. "Silk Touch Transformation" brochures, published in the United States in Jan. 1995, 4 pages.

Sharplan Lasers, Inc. "Sharplan 771 Microscan" brochure, published in the United States in Jan. 1995, 3 pages.

Sharplan Laser, Inc. "Sharplan 771 General System Description" brochure, published in the United States in Jan. 1995, 17 pages.

Sharplan Lasers, Inc. "Sharplan 775A/B System Description" brochure, published in the United States in Jan. 1995, 23 pages.

Sharplan Lasers, Inc. "Sharplan 775" brochure, published in the United States in Jan. 1995, 2 pages.

Sharplan Lasers, Inc. "Sharplan 775/776/777 Microscan" brochure, published in the U. S. in Jan. 1995, 2 pages.

Michael Slatkine, PhD, Yosef P. Krespi, MD; *Instrumentation for Office Laser Surgery*; Operative Techniques in Otolaryngology–Head and Neck Surgery, vol. 5, No. 4, Dec. 1994, pp. 211–217.

Aesthetic $CO_2$ Laser System literature, Aug. 1994; 2 pages.

R. Rox Anderson and John A. Parrish; *Selective Photothermolysis: Precise Microsurgery by Selective Absorption of Pulsed Radiation*; American Association for the Advancement of Science, 29 April 1983, vol. 220, pp. 524–527.

Andrew Blitzer, M.D., *Laser Photocoagulation in the Care of Patients with Osler–Weber–Rendu Disease*, Operative Techniques in Otolaryngology–Head and Neck Surgery, vol. 5, No. 4, Dec. 1994, pp. 274–277.

Arielle Kauvar, M.D., *Laser Therapy for Cutaneous Vascular Lesions*, Operative Techniques in Otolaryngology–Head and Neck Surgery, vol. 5, No. 4, Dec. 1994, pp. 250–258.

LASER FACIAL REJUVENATION

This is a Division of application Ser. No. 08/382,918, filed Feb. 3, 1995,now U.S. Pat. No. 5,611,795.

BACKGROUND

The present invention achieves rejuvenation of skin with minimal thermal damage and carbonization to the papillary dermis. Indications include the smoothing or rejuvenation of perioral, lips and periorbital wrinkles, among others.

Current treatments of the skin surface, whether for cosmetic or clinical applications, have not proven satisfactory. The most common current modalities of skin rejuvenation, namely chemical peeling and mechanical dermabrasion, suffer from lack of depth control and predictability. In addition, dermabrasion may result in bleeding which sends blood particles air-borne. Chemical peeling has the additional drawbacks of possible continued acid penetration after the chemicals are washed away and hypopigmentation.

SUMMARY OF THE INVENTION

A method of smoothing or rejuvenating a predetermined area of human skin is provided comprising ablating the epidermal layer of a predetermined area of human skin with a laser beam and further ablating a portion of the dermal layer originally underlying said ablated epidermal layer to above the papillary dermis. The method further comprises cleaning the area ablated to provide a clean ablated area and protecting the clean ablated area.

The method of smoothing a predetermined area of human skin involves, moreover, irradiating a portion of a predetermined area of human skin with a laser beam for a predetermined scan time to above the papillary dermis, irradiating a next portion of said predetermined area of human skin for said predetermined scan time to above the papillary dermis; and repeating the second and third steps such that the irradiating causes ablation of the skin uniformly.

An objective of the present invention is to provide a method of facial rejuvenation which achieves depth control of ablation to above the papillary dermis with minimal thermal damage.

A further objective of the present invention is to provide a method of smoothing raised areas of skin which achieves depth control of ablation to above the papillary dermis with minimal thermal damage.

BREIF DESCRIPTION OF THE DRAWING

FIG. 1 depicts a fiber through which a laser beam may travel.

DETAILED DESCRIPTION OF THE INVENTION

Figure 1:
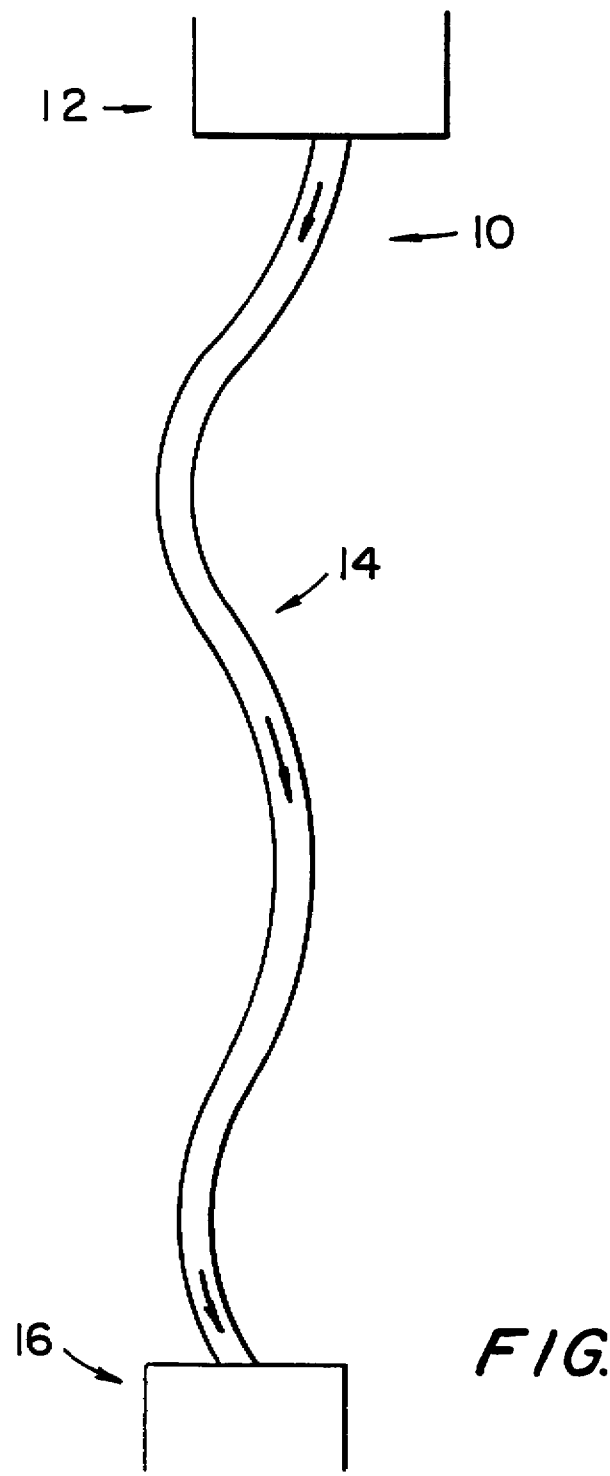

A laser beam is employed to rejuvenate or smooth the skin.

The present invention utilizes a laser preferably in conjunction with a flash scanner system. Flash scanner systems are described in U.S. Pat. application No. 08/175,980entitled "A System for Causing Ablation of Irradiated Material of Living Tissue While Not Causing Damage Below a Predetermined Depth" which has been allowed at this writing, and in the U.S. patent application filed on Dec. 19, 1994 entitled "Method and Apparatus for Applying Laser Beam to a Working Surface, Particularly for Ablating Tissue"(no U.S. Ser. No. issued as yet). The flash scanner contains reflectors such as mirrors or prisms to reflect laser beams of light. The movements of the flash scanner are generally microprocessor controlled to provide the desired pattern of irradiation. The carbon dioxide laser is preferable for the uniform ablation of irradiated material. The laser beam of light may be emitted from articulated arm or, as provided herein, an optical waveguide. A focused or slightly defocused beam may be used.

Preferably, the beam travels through an optical waveguide before reaching the flash scanner. FIG. 1 depicts such an optical waveguide 10 through which a laser beam may travel. The laser beam is generated at laser source 12 and travels through the optical waveguide 14 in the direction of the arrows to the flash scanner 16 containing the reflector system. The optical waveguide, which is loosely referred to as a fiber, provides superior waveguide capability for the laser beam. It also participates in defocusing the laser beam. After passing through the flash scanner, the laser beam is emitted to irradiate the skin surface (not shown here).

The present invention permits all irradiated skin to be ablated with negligible thermal damage and char to the underlying skin. Moreover, any residual thermal damage is shallow and controlled.

The use of flash scanning in facial rejuvenation enables the smoothing of raised areas of the skin such as wrinkle shoulders around the mouth and eyes as well as scars and warts. The epidermal areas and underlying dermal layers are vaporized layer by layer. The treatment can be performed using a predetermined pattern of a spiral pattern or Lissajous figures. A spiral pattern is preferable for skin resurfacing as homogeneous vaporization is particularly desirable for cosmetic or aesthetic surgeries. As described herein, the flash scanner is preferably used in conjunction with scanning for a predetermined scan time.

The method of the present invention provides that the entire epidermal layer of skin of the affected area is ablated. Then ablation proceeds to the papillary dermal layer to a depth of about 70–200 microns, to above the collagen producing cells of the papillary dermis. At typical 7 watt laser operating power, for instance, depth is typically 70 microns with residual thermal damage to the subjacent dermis as low as 75–100 microns. The minimal thermal necrosis resulting to this portion of the dermal layer permits collagen production for smoothing out the skin so as to provide sufficient healing with substantially permanent results. Such favorable cosmetic or aesthetic treatments on otherwise healthy tissue is made possible by this technique.

Rapid movement of the beam over the tissue ensures a 1–2 millisecond short duration of exposure on individual sites within the area. This is shorter than the thermal relaxation time of tissue for laser beam penetration depth of 30 micron at $10.6\mu$ wavelength. The desired scan time is preprogrammed. Irradiation proceeds beginning at another location with minimal overlapping. In this manner the depth of irradiation can be accurately predetermined. The spot size of the laser beam on the skin may be from somewhat less than 0.20 mm diameter to 0.6 mm diameter. The area treated may, for instance, be up to 6 or 9 mm in diameter, with power requirements increasing accordingly.

Advantageously, no bleeding results from the treatment. Following ablation, residual coagulated gray epidermal tissue is wiped off with sterile, saline soaked gauze to expose the dermal layer which is then protected and moisturized with dressings.

The method of the present invention is optimal for facial rejuvenation, for example, the smoothing of wrinkles. The method may also be used for skin rejuvenation as may be contemplated by those skilled in the art.

EXAMPLE

In the following manner the single layer vaporization depth was quantitatively estimated. A $CO_2$ laser was used in clinical cases which generated a focused beam somewhat less than 0.2 mm diameter on tissue. Using the laser at a power level of 7W for facial rejuvenation will generate an optical power density of above 100 $W/mm^2$ on tissue. This is considerably higher than the threshold for vaporization of tissue without residual carbon particles (the threshold for char-free tissue ablation is about 50 $W/mm^2$). The time required to homogeneously cover a round area was programmed to be 200 msec. During this time, the 7 W operating laser delivers 1400 mJ to the tissue. Since the typical energy required to completely ablate tissue is about 3000 mJ for 1 $mm^3$ volume, keeping the facial skin resurfacing handpiece precisely on a single site for 0.2 sec will generate a clean char-free crater of less than 70 micrometer depth for 3 mm diameter scanned area. Minimal residual thermal reaction resulted to the papillary an reticular dermis. No damage occurred to adnexal structures. Histologies of excised facial skins ablated as described also showed that the thermal subcrater necrosis depth was less than 150 $\mu m$.

Over 50 skin exfoliations were performed to smooth out perioral, lip and periorbital wrinkles and scars. The laser power level was set to approximately 7 Watts, although the precise power level selected depended on the skin thickness in conjunction with skin darkness and hair color. In treating wrinkles, the "shoulders" were ablated along both sides of the wrinkles by spiral pattern with caution to avoid overlapping treatment spots and thus avoid ablation of the papillary dermis. The laser repeat mode was used with the laser set to 0.2 sec "on time" and 0.4 sec "off time." Following ablation, residual coagulated gray epidermal tissue was wiped off with sterile, saline soaked gauze to expose the dermal layer which was then protected and moisturized with dressings. Full healing was attained within three months. No permanent hyer- or hypo- pigmentation was observed, although the skin appeared characteristically "pink" for about six weeks.

The entire procedure may be done in an office setting under local anesthesia and lasts 20 minutes on average.

What is claimed is:

1. An apparatus to smooth a predetermined area of human skin comprising:

a laser operative to generate a laser beam that ablates the epidermal layer of said predetermined area of human skin; and that further ablates a portion of the dermal layer originally underlying said ablated epidermal layer to above the papillary dermis;

a scanner through which the laser beam passes and which directs the laser beam so that the laser beam ablates the epidermal layer and further ablates the portion of the dermal layer; and, an optical waveguide intermediate said laser and said scanner for directing the laser beam from said laser to said scanner.

2. An apparatus as claimed in claim 1, in combination with:

a sterile, saline soaked gauze adapted for cleaning the area ablated to provide a clean ablated area; and dressings protecting said clean ablated area.

3. An apparatus as claimed in claim 1, wherein said laser is a carbon dioxide laser.

4. An apparatus as claimed in claim 1, wherein said laser is configured to generate said laser beam to ablate the dermal layer to a depth of between about 70–200 microns.

5. An apparatus as claimed in claim 1, wherein said scanner is adapted to direct said laser beam to expose individual sites within an area of the skin to be ablated for 1–2 milliseconds per scan.

6. An apparatus to smooth a predetermined area of human skin comprising:

a laser generating a laser beam that irradiates a portion of said predetermined area of human skin for a predetermined scan time to ablate the epidermal layer of said portion of said predetermined area of human skin and to further ablate the dermal layer of said portion of said predetermined area of human skin originally underlying said epidermal layer to above the papillary dermis;

said laser being further operative to irradiate with the laser beam a next portion of said predetermined area of human skin for said predetermined scan time to ablate the epidermal layer of said next portion of said predetermined area of human skin and to further ablate the dermal layer of said next portion of said predetermined area of human skin originally underlying said epidermal layer to above the papillary dermis, said laser being further operative so that irradiation causes ablation of said skin that is uniform;

a scanner through which the laser beam passes and which directs the laser beam so that the laser beam ablates the epidermal layer and further ablates the portion of the dermal layer, and, an optical waveguide intermediate said laser and said scanner for directing the laser beam from said laser to said scanner.

7. An apparatus as claimed in claim 6, wherein said laser is a carbon dioxide laser.

8. An apparatus as claimed in claim 6, wherein said laser is configured to generate said laser beam to ablate the dermal layer to a depth of between about 70–200 microns.

9. An apparatus as claimed in claim 6, wherein said scanner directs said laser beam to expose individual sites within an area of the skin to be ablated for 1–2 milliseconds per scan.

* * * * *